United States Patent
Seneca et al.

(10) Patent No.: US 11,253,459 B2
(45) Date of Patent: *Feb. 22, 2022

(54) DYE COMPOSITION BASED ON COPOLYMERS DERIVED FROM THE POLYMERIZATION OF AT LEAST ONE CROTONIC ACID MONOMER OR CROTONIC ACID DERIVATIVE AND OF AT LEAST ONE THICKENING POLYMER BEARING (METH)ACRYLIC ACID UNIT(S), AND PROCESS FOR DYEING KERATIN FIBERS USING SAME

(71) Applicant: L'OREAL, Paris (FR)

(72) Inventors: David Seneca, Saint-Ouen (FR); Delphine Charrier, Saint-Ouen (FR); Sophie Bodelin, Chevilly la Rue (FR); Malayphone Sananikone, Saint-Ouen (FR); Charlotte Delostal, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/611,825

(22) PCT Filed: May 4, 2018

(86) PCT No.: PCT/EP2018/061581
§ 371 (c)(1),
(2) Date: Nov. 7, 2019

(87) PCT Pub. No.: WO2018/206456
PCT Pub. Date: Nov. 15, 2018

(65) Prior Publication Data
US 2020/0163862 A1 May 28, 2020

(30) Foreign Application Priority Data
May 12, 2017 (FR) ...................................... 1754195

(51) Int. Cl.
*A61K 8/81* (2006.01)
*A61Q 5/06* (2006.01)
(52) U.S. Cl.
CPC .......... *A61K 8/8147* (2013.01); *A61K 8/8135* (2013.01); *A61K 8/8152* (2013.01); *A61Q 5/065* (2013.01); *A61K 2800/43* (2013.01); *A61K 2800/48* (2013.01)
(58) Field of Classification Search
CPC .. A61K 8/8147; A61K 8/8135; A61K 8/8152; A61K 2800/43; A61K 2800/48; A61Q 5/065
See application file for complete search history.

(56) References Cited

U.S. PATENT DOCUMENTS

| | | |
|---|---|---|
| 2,798,053 A | 7/1957 | Brown |
| 2,923,692 A | 2/1960 | Ackerman et al. |
| 3,579,629 A | 5/1971 | Pasero et al. |
| 3,810,977 A | 5/1974 | Levine et al. |
| 3,966,403 A | 6/1976 | Papantoniou et al. |
| 3,966,404 A | 6/1976 | Papantoniou et al. |
| 4,185,087 A | 1/1980 | Morlino |
| 4,237,243 A | 12/1980 | Quack et al. |
| 4,282,203 A | 8/1981 | Jacquet et al. |
| 4,578,266 A | 3/1986 | Tietjen et al. |
| 4,957,732 A | 9/1990 | Grollier et al. |
| 5,645,609 A | 7/1997 | Andrean et al. |
| 5,955,003 A | 9/1999 | Terren et al. |
| 5,990,479 A | 11/1999 | Weiss et al. |
| 6,106,577 A | 8/2000 | Audousset et al. |
| 6,159,486 A | 12/2000 | Terren et al. |
| 6,225,198 B1 | 5/2001 | Alivisatos et al. |
| 8,105,393 B2 | 1/2012 | Suddaby et al. |
| 2004/0170588 A1 | 9/2004 | Bara et al. |
| 2005/0063933 A1 | 3/2005 | Vrignaud et al. |

(Continued)

FOREIGN PATENT DOCUMENTS

| | | |
|---|---|---|
| EP | 0186507 A2 | 7/1986 |
| EP | 0342834 A2 | 11/1989 |

(Continued)

OTHER PUBLICATIONS

Dabbousi, B.O., et al., "(CdSe)ZnS Core-Shell Quantum Dots: Synthesis and Characterization of a Size Series of Highly Luminescent Nanocrystallites," Journal of Physical Chemistry B, vol. 101, 1997, pp. 9463-9475.

Davies, J.T., "A Quantitative Kinetic Theory of Emulsion Type. I. Physical Chemistry of the Emulsifying Agent," Reprinted from: Gas/Liquid and Liquid/Liquid Interfaces, Proceedings of 2nd International Congress Surface Activity, Butterworths, London, 1957, pp. 426-438.

Godfrey, K.M., "Cationic Emulsifiers in Cosmetics," J. Soc. Cosmetic Chemists, 17, (1966), pp. 17-27.

(Continued)

*Primary Examiner* — Quanglong N Truong
(74) *Attorney, Agent, or Firm* — The Marbury Law Group, PLLC

(57) ABSTRACT

The present invention relates to a composition for dyeing keratin fibers, comprising at least (i) one or more copolymers derived from the polymerization of at least one crotonic acid monomer or crotonic acid derivative and of at least two different vinyl ester monomers, (ii) one or more thickening polymers bearing (meth)acrylic acid unit(s), and (iii) one or more pigments. The invention also relates to a dyeing process in which said composition is applied to keratin fibers, the operation optionally being followed by drying. The composition makes it possible to obtain temporary dyeing having the advantage of forming a transfer-resistant deposit, leaving the treated fibers individualized, with an improved cosmetic feel.

15 Claims, No Drawings

(56) References Cited

U.S. PATENT DOCUMENTS

| | | | |
|---|---|---|---|
| 2005/0226838 A1* | 10/2005 | Krause | A61K 8/736 424/70.13 |
| 2007/0224145 A1 | 9/2007 | Walter et al. | |
| 2013/0149358 A1 | 6/2013 | Colaco | |
| 2013/0164248 A1* | 6/2013 | Khenniche | A61K 8/8147 424/70.122 |
| 2016/0213598 A1* | 7/2016 | Oh | A61K 8/898 |
| 2020/0163862 A1 | 5/2020 | Seneca et al. | |

FOREIGN PATENT DOCUMENTS

| | | |
|---|---|---|
| EP | 0530974 A1 | 3/1993 |
| EP | 0945130 A2 | 9/1999 |
| EP | 1184426 A2 | 3/2002 |
| FR | 1222944 A | 6/1960 |
| FR | 1564110 A | 4/1969 |
| FR | 1580545 A | 9/1969 |
| FR | 2265781 A1 | 10/1975 |
| FR | 2265782 A1 | 10/1975 |
| FR | 2416723 A1 | 9/1979 |
| FR | 2439798 A1 | 5/1980 |
| FR | 2679771 A1 | 2/1993 |
| FR | 2709418 A1 | 3/1995 |
| FR | 2741530 A1 | 5/1997 |
| FR | 2750601 A1 | 1/1998 |
| FR | 2758719 A1 | 7/1998 |
| GB | 922457 A | 4/1963 |
| JP | 05-017710 A | 1/1993 |
| JP | 07-258460 A | 10/1995 |
| JP | 09-188830 A | 7/1997 |
| JP | H10-502945 A | 3/1998 |
| JP | 10-158450 A | 6/1998 |
| JP | 10-158541 A | 6/1998 |
| JP | 2003-201217 A | 7/2003 |
| JP | 2007-511551 A | 5/2007 |
| WO | 2009/049746 A2 | 4/2009 |
| WO | 2017/108824 A1 | 6/2017 |
| WO | 2018/206453 A1 | 11/2018 |
| WO | 2019/002143 A1 | 1/2019 |

OTHER PUBLICATIONS

Griffin, William C., "Calculation of HLB Values of Non-Ionic Surfactants," J. Soc. Cosmet. Chemists, vol. 5 (1954), pp. 249-256.

Mintel, "Cover Hair Root Retouch Concealer Spray," CCD Cosmetica Cientifica Dermatologica, XP002776566, Dec. 2016.

Peng, Xiaogang et al., "Epitaxial Growth of Highly Luminescent CdSe/CdS Core/Shell Nanocrystals with Photostability and Electronic Accessibility," Journal of the American Chemical Society, vol. 119, No. 30, 1997, pp. 7019-7029.

Puisieux, F., et al., Galencia 5: Les systèmes dispersés—Tome 1—Agents de surface et emulsions—Chapitre IV—Notions de HLB et du HLB critique, pp. 153-194—paragraph 1.1.2 Détermination de HLB par voie expérimental [Experimental determination of HLB], published by Technique et Documentation (Lavoisier), 1983, pp. 164-180.

Mintel, "Hair Spray," Baston do Brasil Produtos Quimicos, XP002773537, Sep. 2016.

Todd, Charles, et al., "Volatile Silicone Fluids for Cosmetic Formulations," Cosmetics and Toiletries, vol. 91, Jan. 1976, pp. 29-32.

International Search Report and Written Opinion for counterpart Application No. PCT/EP2018/61575, dated Jun. 20, 2018.

International Search Report and Written Opinion for counterpart Application No. PCT/EP2018/061581, dated Jul. 2, 2018.

International Search Report and Written Opinion for counterpart Application No. PCT/EP2018/066801, dated Aug. 16, 2018.

Translated Notice of Reasons for Refusal for counterpart Japanese Application No. 2019-555650, dated Oct. 12, 2020.

Translated Notice of Reasons for Refusal for counterpart Japanese Application No. 2020-503366, dated Nov. 2, 2020.

Non-Final Office Action for copending U.S. Appl. No. 16/611,787, dated Sep. 25, 2020.

Final Office Action for copending U.S. Appl. No. 16/611,787, dated Mar. 23, 2021.

Non-Final Office Action for copending U.S. Appl. No. 16/611,787, dated Sep. 9, 2021.

Direct Dye Britannica Online Encyclopedia, Jul. 20, 1998.

* cited by examiner

DYE COMPOSITION BASED ON COPOLYMERS DERIVED FROM THE POLYMERIZATION OF AT LEAST ONE CROTONIC ACID MONOMER OR CROTONIC ACID DERIVATIVE AND OF AT LEAST ONE THICKENING POLYMER BEARING (METH)ACRYLIC ACID UNIT(S), AND PROCESS FOR DYEING KERATIN FIBERS USING SAME

CROSS REFERENCE TO RELATED APPLICATION

This is a national stage application of PCT/EP2018/061581, filed internationally on May 4, 2018, which claims priority to French Application No. 1754195, filed on May 12, 2017, both of which are incorporated by reference herein in their entireties.

The present invention relates to a composition for dyeing keratin fibers, comprising at least one copolymer derived from the polymerization of at least one crotonic acid monomer or crotonic acid derivative and of at least one vinyl ester monomer, at least one thickening polymer bearing (meth)acrylic acid unit(s), and at least one pigment, and also to a dyeing process using said composition.

In the field of dyeing keratin fibers, in particular human keratin fibers, it is already known practice to dye keratin fibers via various techniques using direct dyes or pigments for non-permanent dyeing, or dye precursors for permanent dyeing.

There are essentially three types of process for dyeing the hair:

a) "permanent" dyeing, the function of which is to afford a substantial modification to the natural color and which uses oxidation dyes which penetrate into the hair fiber and form the dye via an oxidative condensation process;

b) non-permanent, semi-permanent or direct dyeing, which does not use the oxidative condensation process and withstands four or five shampoo washes; it consists in dyeing keratin fibers with dye compositions containing direct dyes. These dyes are colored and coloring molecules that have affinity for keratin fibers.

c) temporary dyeing, which gives rise to a modification of the natural color of the hair that remains from one shampoo washing to the next, and which serves to enhance or correct a shade that has already been obtained. It may also be likened to a "makeup" process.

For this last type of dyeing, it is known practice to use colored polymers formed by grafting one or more dyes of azo, triphenylmethane, azine, indoamine or anthraquinone nature onto a polymer chain. These colored polymers are not entirely satisfactory, especially as regards the homogeneity of the coloring obtained and its resistance, not to mention the problems associated with their manufacture and especially with their reproducibility.

Another dyeing method consists in using pigments. Specifically, the use of pigment on the surface of keratin fibers generally makes it possible to obtain visible colorings on dark hair, since the surface pigment masks the natural color of the fiber. The use of pigment for dyeing keratin fibers is described, for example, in patent application FR 2 741 530; when they are applied to keratin fibers, these compositions have the drawback of transferring, i.e. of becoming at least partly deposited, leaving marks, on certain supports with which they may come into contact and in particular clothing or the skin. This results in mediocre persistence of the applied film, making it necessary to regularly repeat the application of the composition. Moreover, the appearance of these unacceptable marks may put certain people off using this type of dyeing.

Compositions for temporarily dyeing and/or making up the hair may also lead to a hair feel that is uncosmetic and/or not natural; the hair thus dyed may in particular lack softness and/or suppleness and/or individualization.

There is thus still a need to obtain compositions for the temporary dyeing of keratin materials, especially the hair, which have the advantage of forming a transfer-resistant deposit, which in particular does not become deposited, at least partly, onto supports with which said compositions are placed in contact, such as the skin (in particular the hands and the face) and/or clothing.

The invention is directed toward providing compositions which do not degrade keratin fibers, which do not impair their cosmetic properties such as softness and suppleness, keep the hair strands clearly individualized, and do not have a coarse feel, while at the same time having transfer-resistance properties. Furthermore, the compositions according to the invention have good working qualities such as the ease of application and of localization without running.

This aim is achieved with the present invention, one subject of which is a composition for dyeing keratin fibers, especially human keratin fibers such as the hair, comprising at least one copolymer derived from the polymerization of at least one crotonic acid monomer or crotonic acid derivative and of at least two different vinyl ester monomers, at least one thickening polymer bearing (meth)acrylic acid unit(s) and at least one pigment.

Moreover, the presence of pigments or nacres within an aqueous gel may lead to problems of stability of the product; the reason for this is that these pigments and/or nacres are solid particles that are not dissolved in the final composition. As a result, they are liable to interfere with the stability of said composition.

The Applicant has discovered, unexpectedly, that a keratin fiber dye composition comprising at least one copolymer derived from the polymerization of at least one crotonic acid monomer or crotonic acid derivative and of at least two different vinyl ester monomers, at least one thickening polymer bearing (meth)acrylic acid unit(s), makes it possible to produce aqueous gels comprising pigments and/or nacres, these gels moreover being homogeneous and stable, and being able to be applied easily by finger or with any other support.

A subject of the invention is also a process for dyeing keratin fibers, especially human keratin fibers such as the hair, comprising the application to said fibers of a composition as defined above.

The term "at least one" means "one or more".

The term "comprising a" means "comprising at least one", unless otherwise specified.

One subject of the present invention is thus a composition for dyeing keratin fibers, especially human keratin fibers such as the hair, comprising (i) one or more copolymers derived from the polymerization of at least one crotonic acid monomer or crotonic acid derivative and of at least two different vinyl ester monomers, (ii) one or more thickening polymers bearing (meth)acrylic acid unit(s) and (iii) one or more pigments.

Dye Composition

The composition according to the invention is preferably a cosmetic composition for dyeing keratin fibers, in particular human keratin fibers such as hair.

It has been observed that by using the composition according to the invention, it is possible to improve the individualization of the hair strands, and also to reduce the transfer. The fibers also have a smoother feel, are softer and more supple, and disentangle more easily. Furthermore, this composition makes it possible to obtain a smooth, glossy gel of suitable viscosity for easy and localized application.

Crotonic Acid Copolymers

The composition according to the invention comprises at least one copolymer derived from the polymerization of at least one crotonic acid monomer or crotonic acid derivative and of at least two different vinyl ester monomers.

The copolymer according to the invention is chosen from copolymers derived from the polymerization of at least one crotonic acid monomer and of at least two different vinyl ester monomers.

The term "crotonic acid derivative" preferably means a crotonic acid ester or a crotonic acid amide.

The term "crotonic acid derivative" preferably means a crotonic acid ester or amide, in particular:
(i) the crotonic acid esters of formula $CH_3CH=CHCOOR'1$ with R'1 representing a linear, branched or cyclic, saturated or unsaturated, optionally aromatic (aryl, aralkyl or alkylaryl) carbon-based and especially hydrocarbon-based (alkyl) chain, containing 1 to 30 carbon atoms, optionally comprising one or more functions chosen from —OH, —OR' with R' C1-C6 alkyl (alkoxy), —CN, —X (halogen, especially Cl, F, Br or I); mention may be made, for example, of methyl crotonate and ethyl crotonate
(ii) the crotonic acid amides of formula $CH_3CH=CHCONR'2R''2$ with R'2 and R''2, which may be identical or different, representing hydrogen or a linear, branched or cyclic, saturated or unsaturated, optionally aromatic, carbon-based and especially hydrocarbon-based (alkyl) chain, containing 1 to 30 carbon atoms, optionally comprising one or more functions chosen from —OH, —OR' with R' C1-C6 alkyl (alkoxy), —CN, —X (halogen, especially Cl, F, Br or I).

The term "crotonic acid derivative" preferably means a crotonic acid ester or amide, in particular:
(i) the crotonic acid esters of formula $CH_3CH=CHCOOR'1$ with R'1 representing a linear, branched or cyclic, saturated or unsaturated, optionally aromatic such as an aryl, aralkyl or alkylaryl, carbon-based and especially hydrocarbon-based chain such as an alkyl, containing 1 to 30 carbon atoms, optionally comprising one or more functions chosen from —OH, —OR' with R' C1-C6 alkyl such as an alkoxy, —CN, —X such as a halogen, especially Cl, F, Br or I; mention may be made, for example, of methyl crotonate and ethyl crotonate,
(ii) the crotonic acid amides of formula $CH_3CH=CHCONR'2R''2$ with R'2 and R''2, which may be identical or different, representing hydrogen or a linear, branched or cyclic, saturated or unsaturated, optionally aromatic, carbon-based and especially hydrocarbon-based chain such as an alkyl, containing 1 to 30 carbon atoms, optionally comprising one or more functions chosen from —OH, —OR' with R' C1-C6 alkyl such as an alkoxy, —CN, —X such as a halogen, especially Cl, F, Br or I.

The vinyl ester monomer(s) may be chosen from the compounds of formula $CH_2=CH-OCO-R'3$ with R'3 representing a linear, branched or cyclic, saturated or unsaturated, optionally aromatic, carbon-based and especially hydrocarbon-based chain, containing 1 to 30 carbon atoms, optionally comprising one or more functions chosen from —OH, —OR' with R' C1-C6 alkyl (alkoxy), —CN, —X (halogen, especially Cl, F, Br or I).

Mention may be made especially of vinyl acetate, vinyl propionate, vinyl butyrate (or butanoate), vinyl ethylhexanoate, vinyl neononanoate, vinyl neododecanoate, vinyl neodecanoate, vinyl pivalate, vinyl cyclohexanoate, vinyl benzoate, vinyl 4-tert-butylbenzoate and vinyl trifluoroacetate.

The copolymer according to the invention is chosen from copolymers derived from the polymerization of at least one crotonic acid monomer and of at least two different vinyl ester monomers, said vinyl ester monomers preferably being chosen from vinyl acetate, vinyl propionate, vinyl butyrate (or butanoate), vinyl ethylhexanoate, vinyl neononanoate, vinyl neododecanoate, vinyl neodecanoate, vinyl pivalate, vinyl cyclohexanoate, vinyl benzoate, vinyl 4-tert-butylbenzoate and vinyl trifluoracetate, preferably from vinyl acetate, vinyl propionate and vinyl neodecanoate, better still from vinyl acetate and vinyl neodecanoate.

More particularly, the copolymer according to the invention is chosen from copolymers derived from the polymerization of crotonic acid, vinyl acetate and vinyl propionate, copolymers derived from the polymerization of crotonic acid, vinyl acetate and vinyl neodecanoate, and mixtures thereof.

According to a particular embodiment, the copolymer of the composition according to the invention is a crotonic acid/vinyl acetate/vinyl neodecanoate terpolymer.

The copolymers according to the invention may optionally comprise other monomers such as allylic or methallylic esters, or vinyl ethers. These polymers may optionally be grafted or crosslinked.

Such polymers are described, inter alia, in French patent Nos. 1 222 944, 1 580 545, 2 265 782, 2 265 781, 1 564 110 and 2 439 798. Commercial products which fall into this category are the products Resyn® 28-2930 and 28-1310 sold by the company Akzo Nobel (INCI names VA/crotonates/vinyl decanoate copolymer and VA/crotonates copolymer, respectively). Mention may also be made of the products Luviset® CA 66 sold by the company BASF, Aristoflex® A60 sold by the company Clariant (INCI name VA/crotonates copolymer) and Mexomere® PW or PAM sold by the company Chimex (INCI name VA/vinyl butyl benzoate/crotonates copolymer).

The total amount of copolymer(s) of crotonic acid or crotonic acid derivative according to the invention may range from 0.05% to 15% by weight relative to the weight of the composition, preferably from 0.1% to 10% by weight relative to the weight of the composition, preferably from 1% to 5% by weight relative to the weight of the composition.

Thickening Polymers Bearing (Meth)Acrylic Acid Unit(s)

The composition according to the invention comprises at least one thickening polymer bearing acrylic acid and/or methacrylic acid unit(s). The polymer bearing acrylic acid and/or methacrylic acid unit(s) according to the invention may be crosslinked. Preferably, the polymer bearing acrylic acid and/or methacrylic acid unit(s) according to the invention is crosslinked.

According to the present invention, the term "hickening polymer" refers to a polymer which, by its presence at a concentration of 0.05% by weight, increase the viscosity of a composition into which it is introduced by at least 20 cps, preferably by at least 50 cps, at room temperature (25° C.), at atmospheric pressure and at a shear rate of 1 $s^{-1}$ (the viscosity may be measured using a cone/plate viscometer, a Haake R600 rheometer or the like).

As indicated above, the composition contains one or more thickening polymers bearing (meth)acrylic acid unit(s). The thickening polymers bearing (meth)acrylic acid unit(s) may optionally be in salified form.

In particular, the acrylic or methacrylic acid units may be in alkali metal or ammonium acrylate or methacrylate form.

The thickening polymers bearing (meth)acrylic acid unit(s) according to the invention may be anionic or amphoteric, preferably anionic.

The thickening polymers bearing (meth)acrylic acid unit(s) are especially chosen from:
(a) acrylic associative polymers;
(b) preferably crosslinked acrylic acid homopolymers;
(c) crosslinked copolymers of (meth)acrylic acid and of ($C_1$-$C_6$)alkyl acrylate;
(d) ammonium acrylate homopolymers or copolymers of ammonium acrylate and of acrylamide.

According to the invention, the term "associative polymer" means an amphiphilic polymer comprising both hydrophilic units and hydrophobic units, in particular comprising at least one C8-C30 fatty chain and at least one hydrophilic unit.

Preferably, the composition contains an acrylic acid homopolymer, which is preferably crosslinked. Polymers of this type have the INCI name Carbomer.

a) acrylic associative polymers;

Acrylic associative polymers according to the invention that may be used are acrylic associative polymers bearing (meth)acrylic acid unit(s) chosen from:
(i) anionic amphiphilic polymers bearing (meth)acrylic acid unit(s) comprising at least one hydrophilic unit and at least one fatty-chain unit;
(ii) amphoteric amphiphilic polymers bearing (meth)acrylic acid unit(s) comprising at least one hydrophilic unit and at least one fatty-chain unit, the fatty chains containing from 10 to 30 carbon atoms.

In particular, the associative polymers bearing (meth)acrylic acid unit(s) may be chosen from:
Anionic amphiphilic polymers comprising at least one hydrophilic unit of (meth)acrylic acid type and at least one hydrophobic unit of ($C_{10}$-$C_{30}$)alkyl ester of unsaturated carboxylic acid type,
amphoteric amphiphilic polymers comprising at least one hydrophilic unit of (meth)acrylic acid type and containing at least one fatty chain, such as copolymers of methacrylamidopropyltrimethylammonium chloride/acrylic acid/C10-C30 alkyl methacrylate, the alkyl radical preferably being a stearyl radical.

b) preferably crosslinked acrylic acid homopolymers.

The polymer may be crosslinked with a crosslinking agent, in particular chosen from pentaerythritol allyl ether, sucrose allyl ether, or propylene allyl ether. Such polymers have the INCI name: Carbomer. Use may be made, for example, of the polymers sold by the company Lubrizol under the names Carbopol 980 or 981, or Carbopol Ultrez 10, or by the company 3V under the name Synthalen K or Synthalen L or Synthalen M.

c) crosslinked copolymers of (meth)acrylic acid and of ($C_1$-$C_6$)alkyl acrylate;

Among the crosslinked copolymers of (meth)acrylic acid and of $C_1$-$C_6$ alkyl acrylate that may be mentioned is the product sold under the name Viscoatex 538C by the company Coatex, which is a crosslinked copolymer of methacrylic acid and of ethyl acrylate as an aqueous dispersion containing 38% active material, or the product sold under the name Aculyn 33 by the company Röhm & Haas, which is a crosslinked copolymer of acrylic acid and of ethyl acrylate as an aqueous dispersion containing 28% active material. Mention may be made more particularly of the crosslinked methacrylic acid/ethyl acrylate copolymer in the form of an aqueous 30% dispersion manufactured and sold under the name Carbopol Aqua SF-1 by the company Noveon.

d) ammonium acrylate homopolymers or copolymers of ammonium acrylate and of acrylamide;

Among the ammonium acrylate homopolymers that may be mentioned is the product sold under the name Microsap PAS 5193 by the company Hoechst.

Among the copolymers of ammonium acrylate and of acrylamide that may be mentioned is the product sold under the name Bozepol C Nouveau or the product PAS 5193 sold by the company Hoechst (they are described and prepared in FR-2 416 723, U.S. Pat. Nos. 2,798,053 and 2,923,692).

According to a particular embodiment of the invention, the composition comprises at least one crosslinked acrylic and/or methacrylic acid thickening polymer.

According to a particular embodiment of the invention, the composition comprises at least one thickening polymer bearing (meth)acrylic acid unit(s) chosen from crosslinked acrylic acid homopolymers.

According to the invention, the thickening polymer(s) bearing (meth)acrylic acid unit(s) may represent from 0.001% to 20% by weight, preferably from 0.01% to 10% by weight and more particularly from 0.1% to 5% by weight, better still from 0.4% to 2% by weight relative to the total weight of the final composition.

Preferably, the weight ratio of the total amount of copolymer(s) of crotonic acid or crotonic acid derivative according to the invention to the amount of thickening polymer bearing (meth)acrylic acid unit(s) ranges from 0.1 to 15, more preferentially from 1 to 10 and better still from 2 to 8.

Pigments

The composition comprises one or more pigments.

The term "pigment" is understood to mean white or colored particles of any shape which are insoluble in the composition in which they are present.

The pigments that may be used are especially chosen from the organic and/or mineral pigments known in the art, especially those described in Kirk-Othmer's Encyclopedia of Chemical Technology and in Ullmann's Encyclopedia of Industrial Chemistry.

They may be natural, of natural origin, or not.

These pigments may be in pigment powder or paste form. They may be coated or uncoated.

The pigments may be chosen, for example, from mineral pigments, organic pigments, lakes, pigments with special effects, such as nacres or glitter flakes, and mixtures thereof.

The pigment may be a mineral pigment. The term "mineral pigment" means any pigment that satisfies the definition in Ullmann's encyclopedia in the chapter on inorganic pigments. Mention may be made, among mineral pigments of use in the present invention, of ochres, such as red ochre (clay (in particular kaolinite) and iron hydroxide (for example hematite)), brown ochre (clay (in particular kaolinite) and limonite) or yellow ochre (clay (in particular kaolinite) and goethite); titanium dioxide, optionally surface-treated; zirconium or cerium oxides; zinc, (black, yellow or red) iron or chromium oxides; manganese violet, ultramarine blue, chromium hydrate and ferric blue; or metal powders, such as aluminum powder or copper powder.

Mention may also be made of carbonates of alkaline-earth metals (for example calcium or magnesium), silicon dioxide, quartz, and also any other compound used as inert filler in cosmetic compositions, provided that these compounds afford the composition color or whiteness under the conditions in which they are used.

The pigment may be an organic pigment. The term "organic pigment" means any pigment that satisfies the definition in Ullmann's encyclopedia in the chapter on organic pigments.

The organic pigment may especially be chosen from nitroso, nitro, azo, xanthene, pyrene, quinoline, anthraquinone, triphenylmethane, fluorane, phthalocyanine, metal-complex, isoindolinone, isoindoline, quinacridone, perinone, perylene, diketopyrrolopyrrole, indigo, thioindigo, dioxazine, triphenylmethane and quinophthalone compounds.

Use may also be made of any mineral or organic compound that is insoluble in the composition and standard in the cosmetics field, provided that these compounds give the composition color or whiteness under the conditions under which they are used, for example guanine, which, according to the refractive index of the composition, is a pigment.

In particular, the white or colored organic pigments may be chosen from carmine, carbon black, aniline black, azo yellow, quinacridone, phthalocyanine blue, the blue pigments codified in the Color Index under the references CI 42090, 69800, 69825, 73000, 74100, 74160, the yellow pigments codified in the Color Index under the references CI 11680, 11710, 15985, 19140, 20040, 21100, 21108, 47000, 47005, the green pigments codified in the Color Index under the references CI 61565, 61570, 74260, the orange pigments codified in the Color Index under the references CI 11725, 15510, 45370, 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, 75470, the pigments obtained by oxidative polymerization of indole or phenolic derivatives as described in patent FR 2 679 771.

Examples that may also be mentioned include pigmentary pastes of organic pigments, such as the products sold by the company Hoechst under the names:
  Cosmenyl Yellow 10G: Pigment Yellow 3 (CI 11710);
  Cosmenyl Yellow G: Pigment Yellow 1 (CI 11680);
  Cosmenyl Orange GR: Pigment Orange 43 (CI 71105);
  Cosmenyl Red R: Pigment Red 4 (CI 12085);
  Carmine Cosmenyl FB: Pigment Red 5 (CI 12490);
  Cosmenyl Violet RL: Pigment Violet 23 (CI 51319);
  Cosmenyl Blue A2R: Pigment Blue 15.1 (CI 74160);
  Cosmenyl Green GG: Pigment Green 7 (CI 74260);
  Cosmenyl Black R: Pigment Black 7 (CI 77266).

The pigments in accordance with the invention may also be in the form of composite pigments, as described in patent EP 1 184 426. These composite pigments may be composed especially of particles comprising a mineral core, at least one binder, which provides for the attachment of the organic pigments to the core, and at least one organic pigment which at least partially covers the core.

The organic pigment may also be a lake. The term "lake" means dyes adsorbed onto insoluble particles, the assembly thus obtained remaining insoluble during use.

The mineral substrates onto which the dyes are adsorbed are, for example, alumina, silica, calcium sodium borosilicate or calcium aluminum borosilicate and aluminum.

Among the dyes, mention may be made of carminic acid. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), D&C Blue 1 (CI 42 090).

Mention may be made, as examples of lakes, of the product known under the following name: D&C Red 7 (CI 15 850:1).

The pigment may also be a pigment with special effects. The term "pigments with special effects" means pigments that generally create a colored appearance (characterized by a certain shade, a certain vivacity and a certain level of luminance) that is non-uniform and that changes as a function of the conditions of observation (light, temperature, angles of observation, etc.). They thus contrast with colored pigments that afford a standard uniform opaque, semi-transparent or transparent shade.

Several types of pigment with special effects exist: those with a low refractive index, such as fluorescent or photochromic pigments, and those with a higher refractive index, such as nacres, interference pigments or glitter flakes.

Examples of pigments with special effects that may be mentioned include nacreous pigments such as mica coated with titanium or with bismuth oxychloride, colored nacreous pigments such as mica coated with titanium and with iron oxides, mica coated with iron oxides, mica coated with titanium and especially with ferric blue or with chromium oxide, mica coated with titanium and with an organic pigment of the abovementioned type, and also nacreous pigments based on bismuth oxychloride. Nacreous pigments that may be mentioned include the Cellini nacres sold by Engelhard (mica-TiO2-lake), Prestige sold by Eckart (mica-TiO2), Prestige Bronze sold by Eckart (mica-Fe2O3), and Colorona sold by Merck (mica-TiO2-Fe2O3).

Mention may be made of the gold-colored nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a coppery glint sold especially by the company Engelhard under the name Copper 340A (Timica); the nacres with a red glint sold especially by the company Merck under the name Sienna fine (17386) (Colorona); the nacres with a yellow glint sold especially by the company Engelhard under the name Yellow (4502) (Chromalite); the red nacres with a gold glint sold especially by the company Engelhard under the name Sunstone G012 (Gemtone); the pink nacres sold especially by the company Engelhard under the name Tan opale G005 (Gemtone); the black nacres with a gold glint sold especially by the company Engelhard under the name Nu antique bronze 240 AB (Timica), the blue nacres sold especially by the company Merck under the name Matte blue (17433) (Microna), the white nacres with a silvery glint sold especially by the company Merck under the name Xirona Silver, and the golden-green pink-orange nacres sold especially by the company Merck under the name Indian summer (Xirona), and mixtures thereof.

Still as examples of nacres, mention may also be made of particles comprising a borosilicate substrate coated with titanium oxide.

Particles comprising a glass substrate coated with titanium oxide are sold in particular under the name Metashine MC1080RY by the company Toyal.

Finally, examples of nacres that may also be mentioned include polyethylene terephthalate flakes, especially those sold by the company Meadowbrook Inventions under the name Silver 1P 0.004X0.004 (silver flakes).

It is also possible to envisage multilayer pigments based on synthetic substrates, such as alumina, silica, calcium sodium borosilicate, calcium aluminum borosilicate and aluminum.

The pigments with special effects may also be chosen from reflective particles, i.e. especially from particles whose size, structure, especially the thickness of the layer(s) of which they are made and their physical and chemical nature, and surface state, allow them to reflect incident light. This reflection may, if appropriate, have an intensity sufficient to create, at the surface of the composition or mixture, when the latter is applied to the substrate to be made up, highlight points visible to the naked eye, that is to say more luminous points which contrast with their surroundings by appearing to sparkle.

The reflective particles may be selected so as not to significantly alter the coloring effect generated by the coloring agents with which they are combined, and more particularly so as to optimize this effect in terms of color rendition. They may more particularly have a yellow, pink, red, bronze, orange, brown, gold and/or coppery color or glint.

These particles may have varied forms and may especially be in platelet or globular form, in particular in spherical form.

Irrespective of their form, the reflective particles may or may not have a multilayer structure, and, in the case of a multilayer structure, may have, for example, at least one layer of uniform thickness, especially of a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be made of one or more organic and/or mineral materials.

More particularly, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material.

Reflective particles are described in particular in the documents JP-A-09188830, JP-A-10158450, JP-A-10158541, JP-A-07258460 and JP-A-05017710.

Mention may also be made, still by way of example of reflective particles comprising a mineral substrate coated with a layer of metal, of the particles comprising a borosilicate substrate coated with silver.

Particles comprising a glass substrate coated with silver, in the form of platelets, are sold under the name Microglass Metashine REFSX 2025 PS by Toyal. Particles with a glass substrate coated with nickel/chromium/molybdenum alloy are sold under the name Crystal Star GF 550 and GF 2525 by this same company.

Use may also be made of particles comprising a metal substrate, such as silver, aluminum, iron, chromium, nickel, molybdenum, gold, copper, zinc, tin, magnesium, steel, bronze or titanium, said substrate being coated with at least one layer of at least one metal oxide, such as titanium oxide, aluminum oxide, iron oxide, cerium oxide, chromium oxide, silicon oxides and mixtures thereof.

Examples that may be mentioned include aluminum powder, bronze powder or copper powder coated with $SiO_2$ sold under the name Visionaire by the company Eckart.

Mention may also be made of pigments with an interference effect which are not attached to a substrate, such as liquid crystals (Helicones HC from Wacker) or interference holographic glitter (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

Quantum dots are luminescent semiconductive nanoparticles capable of emitting, under light excitation, irradiation with a wavelength of between 400 nm and 700 nm. These nanoparticles are known from the literature. In particular, they may be synthesized according to the processes described, for example, in U.S. Pat. No. 6,225,198 or 5,990,479, in the publications cited therein and also in the following publications: Dabboussi B. O. et al., "(CdSe)ZnS core-shell quantum dots: synthesis and characterization of a size series of highly luminescent nanocrystallites", Journal of Physical Chemistry B, vol. 101, 1997, pp. 9463-9475, and Peng, Xiaogang et al., "Epitaxial growth of highly luminescent CdSe/CdS core/shell nanocrystals with photostability and electronic accessibility", Journal of the American Chemical Society, vol. 119, No. 30, pp. 7019-7029.

The variety of pigments that may be used in the present invention makes it possible to obtain a wide range of colors, and also particular optical effects such as metallic effects or interference effects.

The size of the pigment used in the cosmetic composition according to the present invention is generally between 10 nm and 200 µm, preferably between 20 nm and 80 µm and even more preferably between 30 nm and 50 µm.

The pigments may be dispersed in the product by means of a dispersant.

The dispersant serves to protect the dispersed particles against their agglomeration or flocculation. This dispersant may be a surfactant, an oligomer, a polymer or a mixture of several thereof, bearing one or more functionalities with strong affinity for the surface of the particles to be dispersed. In particular, they may become physically or chemically attached to the surface of the pigments. These dispersants also contain at least one functional group that is compatible with or soluble in the continuous medium. In particular, 12-hydroxystearic acid esters and C8 to C20 fatty acid esters of polyols such as glycerol or diglycerol are used, such as poly(12-hydroxystearic acid) stearate with a molecular weight of about 750 g/mol, such as the product sold under the name Solsperse 21 000 by the company Avecia, polyglyceryl-2 dipolyhydroxystearate (CTFA name) sold under the reference Dehymyls PGPH by the company Henkel, or polyhydroxystearic acid such as the product sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments used in the cosmetic composition according to the invention may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described especially in Cosmetics and Toiletries, February 1990, Vol. 105, pages 53-64, before being dispersed in the composition in accordance with the invention. These organic agents may be chosen, for example, from waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminum salts of fatty acids, for example aluminum stearate or laurate; metal alkoxides; polyethylene; (meth) acrylic polymers, for example polymethyl methacrylates; polymers and copolymers containing acrylate units; alkanolamines; silicone compounds, for example silicones, polydimethylsiloxanes; organofluorine compounds, for example perfluoroalkyl ethers; fluorosilicone compounds.

The surface-treated pigments that are useful in the cosmetic composition according to the invention may also have been treated with a mixture of these compounds and/or may have undergone several surface treatments.

The surface-treated pigments that are useful in the context of the present invention may be prepared according to surface-treatment techniques that are well known to those skilled in the art, or may be commercially available in the required form.

Preferably, the surface-treated pigments are coated with an organic layer.

The organic agent with which the pigments are treated may be deposited on the pigments by evaporation of solvent, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is especially described in U.S. Pat. No. 4,578, 266.

An organic agent covalently bonded to the pigments will preferably be used.

The agent for the surface treatment may represent from 0.1% to 50% by weight, preferably from 0.5% to 30% by weight and even more preferentially from 1% to 10% by weight relative to the total weight of the surface-treated pigment.

Preferably, the surface treatments of the pigments are chosen from the following treatments:
- a PEG-silicone treatment, for instance the AQ surface treatment sold by LCW;
- a methicone treatment, for instance the SI surface treatment sold by LCW;
- a dimethicone treatment, for instance the Covasil 3.05 surface treatment sold by LCW;
- a dimethicone/trimethyl siloxysilicate treatment, for instance the Covasil 4.05 surface treatment sold by LCW;
- a magnesium myristate treatment, for instance the MM surface treatment sold by LCW;
- an aluminum dimyristate treatment, such as the MI surface treatment sold by Miyoshi;
- a perfluoropolymethylisopropyl ether treatment, for instance the FHC surface treatment sold by LCW;
- an isostearyl sebacate treatment, for instance the HS surface treatment sold by Miyoshi;
- a perfluoroalkyl phosphate treatment, for instance the PF surface treatment sold by Daito;
- an acrylate/dimethicone copolymer and perfluoroalkyl phosphate treatment, for instance the FSA surface treatment sold by Daito;
- a polymethylhydrogenosiloxane/perfluoroalkyl phosphate treatment, for instance the FS01 surface treatment sold by Daito;
- an acrylate/dimethicone copolymer treatment, for instance the ASC surface treatment sold by Daito;
- an isopropyl titanium triisostearate treatment, for instance the ITT surface treatment sold by Daito;
- an acrylate copolymer treatment, for instance the APD surface treatment sold by Daito;
- a perfluoroalkyl phosphate/isopropyl titanium triisostearate treatment, for instance the PF+ITT surface treatment sold by Daito.

Preferably, the pigment is chosen from mineral or mixed mineral-organic pigments.

The amount of pigment(s) may range from 0.01% to 30% by weight, more particularly from 0.05% to 20% by weight, preferably from 0.1% to 15% by weight and preferably from 1% to 10% by weight relative to the total weight of the composition.

The composition of the invention may contain colored or coloring species other than the pigments according to the invention, such as direct dyes or dye precursors.

The composition according to the invention advantageously comprises water, which may preferably be present in a content ranging from 20% to 98% by weight relative to the weight of the composition.

The composition according to the invention may also comprise one or more fatty substances, preferably chosen from silicones and non-silicone fatty substances that are liquid at 30° C. and at atmospheric pressure, better still from silicones and triglyceride oils of plant origin.

When the composition comprises one or more fatty substances, the total content of fatty substances may range from 0.01% to 20% by weight, preferably from 0.05% to 15% by weight and better still from 0.1% to 10% by weight relative to the total weight of the composition.

Additives

The compositions may also comprise at least one agent commonly used in cosmetics, for example chosen from reducing agents, organic solvents, softeners, antifoams, moisturizers, UV-screening agents, peptizers, solubilizers, fragrances, anionic, cationic, nonionic or amphoteric surfactants, proteins and vitamins.

The above additives are generally present in an amount for each of them of between 0.01% and 20% by weight relative to the weight of the composition.

Needless to say, a person skilled in the art will take care to choose this or these optional additive(s) so that the advantageous properties intrinsically attached to the formation of the sheathing in accordance with the invention are not, or not substantially, detrimentally affected.

Presentation Form

The composition according to the invention may especially be in the form of a suspension, a dispersion, a gel, an emulsion, especially an oil-in-water (O/W) or water-in-oil (W/O) emulsion, or a multiple emulsion (W/O/W or polyol/O/W or O/W/O), in the form of a cream, a mousse, a stick, a dispersion of vesicles, especially of ionic or nonionic lipids, or a two-phase or multi-phase lotion. Preferably, the composition is in the form of a gel.

A person skilled in the art may select the appropriate presentation form, and also the method for preparing it, on the basis of his general knowledge, taking into account first the nature of the constituents used, especially their solubility in the support, and secondly the application envisaged for the composition.

Organic Solvents

The composition according to the invention may comprise one or more organic solvents.

Examples of organic solvents that may be mentioned include lower $C_1$-$C_4$ alkanols, such as ethanol and isopropanol; polyols and polyol ethers, for instance 2-butoxyethanol, propylene glycol, propylene glycol monomethyl ether and diethylene glycol monoethyl ether and monomethyl ether, and also aromatic alcohols, for instance benzyl alcohol or phenoxyethanol, and mixtures thereof.

Preferably, the composition according to the invention comprises one or more organic solvents.

When they are present, the organic solvents are present in proportions preferably inclusively between 0.1% and 40% by weight approximately relative to the total weight of the dye composition, more preferentially between 1% and 30% by weight approximately and even more particularly inclusively between 5% and 25% by weight relative to the total weight of the composition.

Process

The composition described above may be used on wet or dry keratin fibers, and also on any type of fair or dark, natural or dyed, permanent-waved, bleached or relaxed fibers.

The application to the fibers may be performed via any standard means, in particular using a comb, a fine brush, a coarse brush or with the fingers.

After application of the composition, the fibers may be left to dry naturally or dried, for example at a temperature above or equal to 30° C. The drying, if it is performed, may be performed immediately after the application. Preferably, if the fibers are dried, they are dried, in addition to supplying heat, with a flow of air.

During drying, a mechanical action may be exerted on the locks, such as combing, brushing or running the fingers through. This operation may similarly be performed once the fibers have been dried, naturally or otherwise.

The drying step of the process of the invention may be performed with a hood, a hair dryer, a straightening iron, a Climazon, etc.

When the drying step is performed with a hood or a hairdryer, the drying temperature is between 30° C. and 110° C. and preferably between 50 and 90° C.

When the drying step is performed with a straightening iron, the drying temperature is between 110 and 220° C. and preferably between 140 and 200° C.

EXAMPLES

Example 1

Compositions (g AM/100 g)

|  | A1 INVENTION |
| --- | --- |
| VA/crotonates/vinyl neodecanoate copolymer | 2 |
| Neutralizer (aminomethylpropanol and/or triethanolamine) | qs |
| Carbomer | 0.75 |
| Mica (and) titanium dioxide | 10 |
| Phenoxyethanol | 0.7 |
| Ethanol | 7.5 |
| PEG-40 Hydrogenated castor oil | 1 |
| *Cocos nucifera* oil | 2 |
| Water | qs 100 |

Protocol

Composition A1 is applied to locks of yack hair at a rate of 1 g of composition per gram of lock. After application, the locks are combed, dried with a hairdryer and then combed again.

Results: "Cosmetic Feel" Performance

The performance qualities in terms of cosmetic feel were evaluated on dried locks by five experts, in a blind test.

In 100% of the cases, the experts judged that composition A1 according to the invention afforded smooth locks with clearly individualized hair strands, having a pleasant cosmetic feel, especially good softness, good suppleness and absence of tackiness.

Example 2

Compositions (g AM/100 g)

|  | A2 Invention | B2 comparative | C2 comparative |
| --- | --- | --- | --- |
| Phenoxyethanol | 0.7 | 0.7 | 0.7 |
| *Cocos nucifera* oil | 2.5 | 2.5 | 2.5 |
| CI 77891 (and) synthetic fluorophlogopite (and) CI 15850 | 10 | 10 | 10 |
| VA/crotonates/vinyl neodecanoate copolymer | 3 | — | — |
| Carbomer | 0.75 | 0.75 | 0.75 |
| Polyvinylcaprolactam | — | 3 | — |
| VP/dimethylaminoethyl methacrylate copolymer | — | — | 3 |
| Ethanol | 7.5 | 7.5 | 7.5 |
| Neutralizer (triethanolamine and/or aminomethylpropanol) | qs | qs | qs |
| PEG-40 Hydrogenated castor oil | 1 | 1 | 1 |
| Water | qs 100 | qs 100 | qs 100 |

Protocol

Composition A2, B2 or C2 is applied to locks of yack hair at a rate of 1 g of composition per gram of lock.

The locks are dried with a hairdryer and then combed.

The locks are then rubbed on a white cloth.

Results: "Transfer-Resistance" Performance

The performance qualities in terms of transfer resistance were evaluated by five experts, in a blind test, who visually evaluated the amount of pigment present on the white cloth after rubbing.

In 100% of the cases, the experts judged that composition A2 according to the invention, compared with compositions B2 and C2, led to a very markedly smaller amount of pigment(s) present on the cloth. Composition A according to the invention thus has better transfer-resistance properties than the comparative compositions B2 and C2.

Example 3

Compositions in Gel Form (g AM/100 g)

|  | A3 INVENTION | C3 COMPAR-ATIVE | D3 COMPAR-ATIVE |
|---|---|---|---|
| VA/crotonates/vinyl neodecanoate copolymer | 2 | 2 | 2 |
| Neutralizer (aminomethylpropanol) | qs | qs | qs |
| Carbomer | 0.5 | — | — |
| Cetylhydroxyethylcellulose | — | 0.5 | — |
| Scleroglucan gum | — | — | 0.5 |
| Mica (and) titanium dioxide | 10 | 10 | 10 |
| Phenoxyethanol | 0.7 | 0.7 | 0.7 |
| Ethanol | 7.5 | 7.5 | 7.5 |
| Water | qs 100 | qs 100 | qs 100 |

Results: "Gel Appearance" Performance

In 100% of the cases, the experts judged that composition A3 of the invention, compared with compositions C3 and D3, led to the production of a smooth, glossy and consistent gel.

Example 4

Compositions (g AM/100 g)

|  | A4 INVENTION | E Comparative |
|---|---|---|
| VA/crotonates/vinyl neodecanoate copolymer | 3 | 3 |
| Neutralizer (aminomethylpropanol and/or triethanolamine) | qs | qs |
| Carbomer | 0.75 | — |
| CI 77891 (and) synthetic fluorphlogopite (and) CI 15850 | 10 | 10 |
| Phenoxyethanol | 0.7 | 0.7 |
| Ethanol | 7.5 | 7.5 |
| PEG-40 Hydrogenated castor oil | 1 | 1 |
| Cocos nucifera oil | 2 | 2 |
| Water | qs 100 | qs 100 |

Protocol

Composition A4 and composition E are applied to locks of yack hair at a rate of 1 g of composition per gram of lock.

After application, the locks are combed, dried with a hairdryer and then combed again.

Results: Performance in Terms of Colour

The performance in terms of homogeneity and intensity of the color are evaluated on dried locks of hair, by 5 experts during a blind test.

100% of the experts have found that the lock of hair treated with composition A4 according to the invention has a more intense and homogeneous color than comparative composition E.

The invention claimed is:

1. A composition for dyeing keratin fibers comprising:
   (i) at least one copolymer derived from the polymerization of at least one crotonic acid monomer or crotonic acid derivative and of at least two different vinyl ester monomers;
   (ii) at least one thickening polymer bearing at least one (meth)acrylic acid unit, chosen from:
      (a) acrylic associative polymers;
      (b) crosslinked acrylic acid homopolymers;
      (c) crosslinked copolymers of (meth)acrylic acid and of (C1-C6)alkyl acrylate; and/or
      (d) ammonium acrylate homopolymers or copolymers of ammonium acrylate and of acrylamide; and
   (iii) at least one pigment.

2. The composition according to claim 1, wherein the at least one crotonic acid derivative is chosen from crotonic acid esters or amides.

3. The composition according to claim 1, wherein the at least one crotonic acid derivative is chosen from crotonic acid esters of formula $CH_3CH\!=\!CHCOOR'1$ with $R'1$ representing a linear, branched or cyclic, saturated or unsaturated, optionally aromatic carbon-based or hydrocarbon-based chain, containing 1 to 30 carbon atoms, optionally comprising at least one function chosen from —OH, —OR' with R' representing C1-C6 alkyl, —CN, or —X halogen.

4. The composition according to claim 1, wherein the at least one crotonic acid derivative is chosen from crotonic acid amides of formula $CH_3CH\!=\!CHCONR'2R''2$ with $R'2$ and $R''2$, which may be identical or different, representing hydrogen or a linear, branched or cyclic, saturated or unsaturated, optionally aromatic, carbon-based or hydrocarbon-based chain, containing 1 to 30 carbon atoms, optionally comprising at least one function chosen from —OH, —OR' with R' representing C1-C6 alkyl, —CN, or —X halogen.

5. The composition according to claim 1, wherein the at least two different vinyl ester monomers are independently chosen from vinyl acetate, vinyl propionate, vinyl butyrate, vinyl ethylhexanoate, vinyl neononanoate, vinyl neodecanoate, vinyl neodecanoate, vinyl pivalate, vinyl cyclohexanoate, vinyl benzoate, vinyl 4-tert-butylbenzoate, or vinyl trifluoroacetate.

6. The composition according to claim 1, wherein the at least one copolymer is chosen from copolymers derived from the polymerization of crotonic acid, vinyl acetate and vinyl propionate, copolymers derived from the polymerization of crotonic acid, vinyl acetate and vinyl neodecanoate, and mixtures thereof.

7. The composition according to claim 1, wherein the at least one copolymer comprises a crotonic acid/vinyl acetate/vinyl neodecanoate terpolymer.

8. The composition according to claim 1, wherein the at least one copolymer further comprises other monomers chosen from allylic esters, methallylic esters, or vinyl ethers.

9. The composition according to claim 1, wherein the at least one copolymer derived from the polymerization of at least one crotonic acid monomer or crotonic acid derivative and of at least two different vinyl ester monomers is present in an amount ranging from 0.05% to 15% by weight, relative to the weight of the composition.

10. The composition according to claim 1, wherein the at least one thickening polymer bearing at least one (meth)acrylic acid unit(s) is crosslinked.

11. The composition according to claim 1, wherein the at least one thickening polymer bearing at least one (meth)acrylic acid unit is chosen from crosslinked acrylic acid homopolymers.

12. The composition according to claim 1, wherein the at least one thickening polymer bearing at least one (meth)acrylic acid unit is present in a total amount from 0.001% to 20% by weight, relative to the total weight of the final composition.

13. The composition according to claim 1, wherein the composition further comprises at least one fatty substance, chosen from silicones and non-silicone fatty substances that are liquid at 30° C. and at atmospheric pressure.

14. A process for the cosmetic treatment of keratin fibers, comprising applying to the fibers a composition comprising:
   (i) at least one copolymer derived from the polymerization of at least one crotonic acid monomer or crotonic acid derivative and of at least two different vinyl ester monomers;
   (ii) at least one thickening polymer bearing at least one (meth)acrylic acid unit, chosen from:
      (a) acrylic associative polymers;
      (b) crosslinked acrylic acid homopolymers;
      (c) crosslinked copolymers of (meth)acrylic acid and of (C1-C6)alkyl acrylate; and/or
      (d) ammonium acrylate homopolymers or copolymers of ammonium acrylate and of acrylamide; and
   (iii) at least one pigment.

15. A process for dyeing human hair comprising applying to the hair a composition comprising:
   (i) at least one copolymer derived from the polymerization of at least one crotonic acid monomer or crotonic acid derivative and of at least two different vinyl ester monomers;
   (ii) at least one thickening polymer bearing at least one (meth)acrylic acid unit, chosen from:
      (a) acrylic associative polymers;
      (b) crosslinked acrylic acid homopolymers;
      (c) crosslinked copolymers of (meth)acrylic acid and of (C1-C6)alkyl acrylate; and/or
      (d) ammonium acrylate homopolymers or copolymers of ammonium acrylate and of acrylamide; and
   (iii) at least one pigment.

* * * * *